(12) United States Patent
Ul-haq et al.

(10) Patent No.: US 12,065,582 B2
(45) Date of Patent: Aug. 20, 2024

(54) CORROSION INHIBITOR SOLUTIONS AND CORROSION-RESISTANT SUBSTRATES THAT INCLUDE BIS-QUATERNIZED AMMONIUM COMPOUNDS AND METHODS OF MAKING THE SAME

(71) Applicant: Saudi Arabian Oil Company, Dhahran (SA)

(72) Inventors: Muhammad Imran Ul-haq, Dhahran (SA); Nayef M. Alanazi, Dhahran (SA); Turki M. Al Abeedi, Dhahran (SA); Abdullah Al-Malki, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/742,004

(22) Filed: May 11, 2022

(65) Prior Publication Data

US 2023/0365815 A1    Nov. 16, 2023

(51) Int. Cl.
  *C09D 5/08*   (2006.01)
  *C07C 211/63*  (2006.01)
  (Continued)

(52) U.S. Cl.
  CPC ............ *C09D 5/086* (2013.01); *C07C 211/63* (2013.01); *C07C 215/40* (2013.01); *C09D 7/45* (2018.01);
  (Continued)

(58) Field of Classification Search
  CPC ......... C23F 11/08; C23F 11/10; C23F 11/149; C23F 11/161; C23F 11/143; F16L 58/04;
  (Continued)

(56) References Cited

U.S. PATENT DOCUMENTS

| | | |
|---|---|---|
| 2,955,083 A | 10/1960 | Levin et al. |
| 3,283,005 A | 11/1966 | Abend et al. |

(Continued)

FOREIGN PATENT DOCUMENTS

| | | |
|---|---|---|
| CA | 2196650 A1 | 8/1998 |
| EP | 1690960 A2 | 8/2006 |

(Continued)

*Primary Examiner* — Yan Lan
(74) *Attorney, Agent, or Firm* — DINSMORE & SHOHL LLP

(57) ABSTRACT

According to embodiments disclosed herein, a corrosion-resistant substrate may comprise a substrate comprising a first surface and a corrosion-resistant film positioned on at least a portion of the first surface of the substrate. A method of producing a corrosion-resistant substrate may comprise contacting at least a portion of a first surface of a substrate with a corrosion inhibitor solution and drying the corrosion inhibitor solution to produce the corrosion-resistant film on the substrate, wherein at least a portion of the solvent may be expelled from the corrosion inhibitor solution during the drying to form the corrosion-resistant film, such that the corrosion-resistant film is solid. The corrosion inhibitor solution and the corrosion-resistant film may comprise a bis-quaternized ammonium compound.

19 Claims, 3 Drawing Sheets

(51) Int. Cl.
  *C07C 215/40* (2006.01)
  *C09D 7/45* (2018.01)
  *C09D 7/63* (2018.01)
  *C23F 11/08* (2006.01)
  *F16L 58/04* (2006.01)

(52) U.S. Cl.
  CPC ............... *C09D 7/63* (2018.01); *C23F 11/08* (2013.01); *F16L 58/04* (2013.01)

(58) Field of Classification Search
  CPC .. F16L 58/1009; C07C 211/63; C07C 215/40; C09D 5/08; C09D 5/086; C09D 7/45; C09D 7/63; C09K 2208/32; C09K 8/04; C09K 8/52; C09K 8/54
  See application file for complete search history.

(56) References Cited

U.S. PATENT DOCUMENTS

| | | | |
|---|---|---|---|
| 3,623,979 A | 11/1971 | Maddox, Jr. et al. | |
| 3,629,104 A | 12/1971 | Maddox, Jr. et al. | |
| 4,515,708 A | 5/1985 | Haslegrave et al. | |
| 4,637,899 A | 1/1987 | Kennedy, Jr. | |
| 4,672,118 A | 6/1987 | Fisk et al. | |
| 4,673,436 A | 6/1987 | Haslegrave et al. | |
| 4,734,277 A | 3/1988 | Login | |
| 4,744,948 A | 5/1988 | Incorvia | |
| 4,784,796 A | 11/1988 | Treybig et al. | |
| 4,812,263 A | 3/1989 | Login | |
| 5,000,873 A | 3/1991 | Fisk et al. | |
| 5,130,034 A | 7/1992 | Williams et al. | |
| 5,292,480 A | 3/1994 | Fischer et al. | |
| 5,336,441 A | 8/1994 | Shah et al. | |
| 5,611,991 A | 3/1997 | Naraghi | |
| 5,756,004 A | 5/1998 | Brezinski | |
| 5,993,693 A | 11/1999 | Meyer | |
| 6,118,000 A | 9/2000 | Frenier | |
| 6,303,079 B1 | 10/2001 | Meyer | |
| 7,057,050 B2 | 6/2006 | Meyer | |
| 7,951,754 B2 | 5/2011 | Tiwari et al. | |
| 9,074,289 B2 | 7/2015 | Malwitz et al. | |
| 9,238,588 B2 | 1/2016 | Harrington et al. | |
| 9,382,467 B2 | 7/2016 | Meyer et al. | |
| 9,434,911 B2 | 9/2016 | Bennett et al. | |
| 9,816,024 B2 | 11/2017 | Jafar Mazumder et al. | |
| 9,868,894 B1 | 1/2018 | Jafar Mazumder et al. | |
| 10,221,368 B2 | 3/2019 | Benitez Aguilar et al. | |
| 10,323,327 B2 | 6/2019 | Obot et al. | |
| 10,604,710 B2 | 3/2020 | Moloney | |
| 2006/0013798 A1 | 1/2006 | Henry et al. | |
| 2010/0219379 A1 | 9/2010 | Acosta et al. | |
| 2013/0233543 A1 | 9/2013 | Overkempe et al. | |
| 2018/0282606 A1 | 10/2018 | Rodgers et al. | |
| 2018/0334750 A1* | 11/2018 | Obot .................. C09K 8/04 | |
| 2020/0318243 A1 | 10/2020 | Obot et al. | |

FOREIGN PATENT DOCUMENTS

| | | | |
|---|---|---|---|
| EP | 3345977 | * | 10/2020 |
| WO | 9933953 A1 | | 7/1999 |
| WO | 2006034101 A1 | | 3/2006 |
| WO | WO2012/063055 | * | 5/2012 |

* cited by examiner

CORROSION INHIBITOR SOLUTIONS AND CORROSION-RESISTANT SUBSTRATES THAT INCLUDE BIS-QUATERNIZED AMMONIUM COMPOUNDS AND METHODS OF MAKING THE SAME

TECHNICAL FIELD

The present disclosure relates to corrosion-resistance and, more specifically, to corrosion-resistant films on substrates formed from corrosion inhibitors.

BACKGROUND

Corrosion is an issue for many materials when they interact with their environments over time. For example, the presence of species such as $H_2S$, $CO_2$, organic acids, and brine solutions in produced oil may create a corrosive environment for transportation pipelines and oil processing units in an oil and gas facility. Specifically, when $CO_2$ and $H_2S$ are dissolved in water, these species may behave like weak acids and promote the corrosion of steel, thus resulting in damage to the internal walls of the transportation pipelines and oil processing units and causing leaks that will increase the maintenance time and costs associated with the oil and gas processing. Many conventional compounds may be used in corrosion-resistant films in order to reduce corrosion of surfaces. However, these conventional compounds are often toxic and non-biodegradable. Additionally, there is a relatively high cost associated with the production of these conventional compounds. Further, these conventional compounds do not sufficiently resist the corrosive effects present in a wet sour environment (i.e., an environment rich in $H_2S$), which are often present in crude oil processing facilities. As such, new compounds are needed in corrosion inhibitors and corrosion-resistant films.

SUMMARY

Described herein are corrosion-resistant films, corrosion-resistant substrates comprising these corrosion-resistant films, and corrosion inhibitor solutions that may be contacted and dried onto surfaces of substrates to create the corrosion-resistant substrates. These corrosion inhibitor solutions and corrosion-resistant films may comprise bis-quaternized ammonium compounds. The presence of these bis-quaternized ammonium compounds in these corrosion inhibitor solutions and corrosion-resistant films may result in relatively strong bonding between the corrosion-resistant films and the substrates and relatively high corrosion-resistant properties in a wet sour environment when compared to conventional compounds adhered to a substrate or a substrate with no corrosion-resistant film. Further, using these bis-quaternized ammonium compounds in the corrosion inhibitor solutions and corrosion-resistant films may reduce the cost associated with the production of corrosion inhibitor solutions and corrosion-resistant films. Also, these bis-quaternized ammonium compounds in the corrosion inhibitor solutions and corrosion-resistant films may be less toxic than conventional compounds present in corrosion inhibitor solutions and corrosion-resistant films.

According to one or more embodiments of the present disclosure, a corrosion-resistant substrate may comprise a substrate comprising a first surface and a corrosion-resistant film positioned on at least a portion of the first surface of the substrate, wherein the corrosion-resistant film may be solid, and wherein the corrosion-resistant film may comprise a bis-quaternized ammonium compound having a general formula:

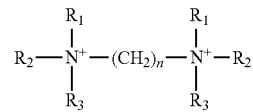

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18.

According to one or more embodiments of the present disclosure, a method of producing a corrosion-resistant substrate comprises contacting at least a portion of a first surface of a substrate with a corrosion inhibitor solution, wherein the corrosion inhibitor solution comprises a solvent and a bis-quaternized ammonium compound and drying the corrosion inhibitor solution to produce the corrosion-resistant film on the substrate, wherein at least a portion of the solvent may be expelled from the corrosion inhibitor solution during the drying to form the corrosion-resistant film, such that the corrosion-resistant film is solid. The bis-quaternized ammonium compound may have the general formula:

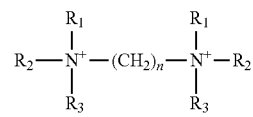

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18.

According to one or more embodiments of the present disclosure, a corrosion inhibitor solution comprises a solvent and a bis-quaternized ammonium compound having a general formula:

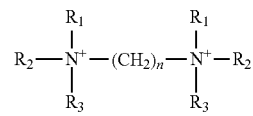

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18.

These and other embodiments are described in more detail in the detailed description. It is to be understood that both the foregoing general description and the following detailed description present embodiments of the presently disclosed technology, and are intended to provide an overview or framework for understanding the nature and character of the presently disclosed technology as it is claimed. The accompanying drawings are included to provide a further understanding of the presently disclosed technology and are incorporated into and constitute a part of this specification. The drawings illustrate various embodiments and, together with the description, serve to explain the principles and operations of the presently disclosed technology. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and wherein.

DETAILED DESCRIPTION

The present disclosure is directed to corrosion-resistant films made from corrosion inhibitor solutions and corrosion-resistant substrates that comprise substrates having a first surface and corrosion-resistant films positioned on at least a portion of the first surface of the substrates.

The corrosion inhibitor solutions and corrosion-resistant films comprise bis-quaternized ammonium compounds.

As described herein, corrosion refers to a process in which a material is oxidized by substances in the environment that causes the material to lose electrons and deteriorates at least a portion of the material. The term "corrosion-resistant" generally refers to the resistance that a material has against corrosion. As described herein, corrosion-resistant materials display enhanced resistance to corrosion on the substrates, which may be achieved, as is describe in embodiments herein, by forming a barrier over the substrates, thus shielding the substrates from the environment.

Figure 1:
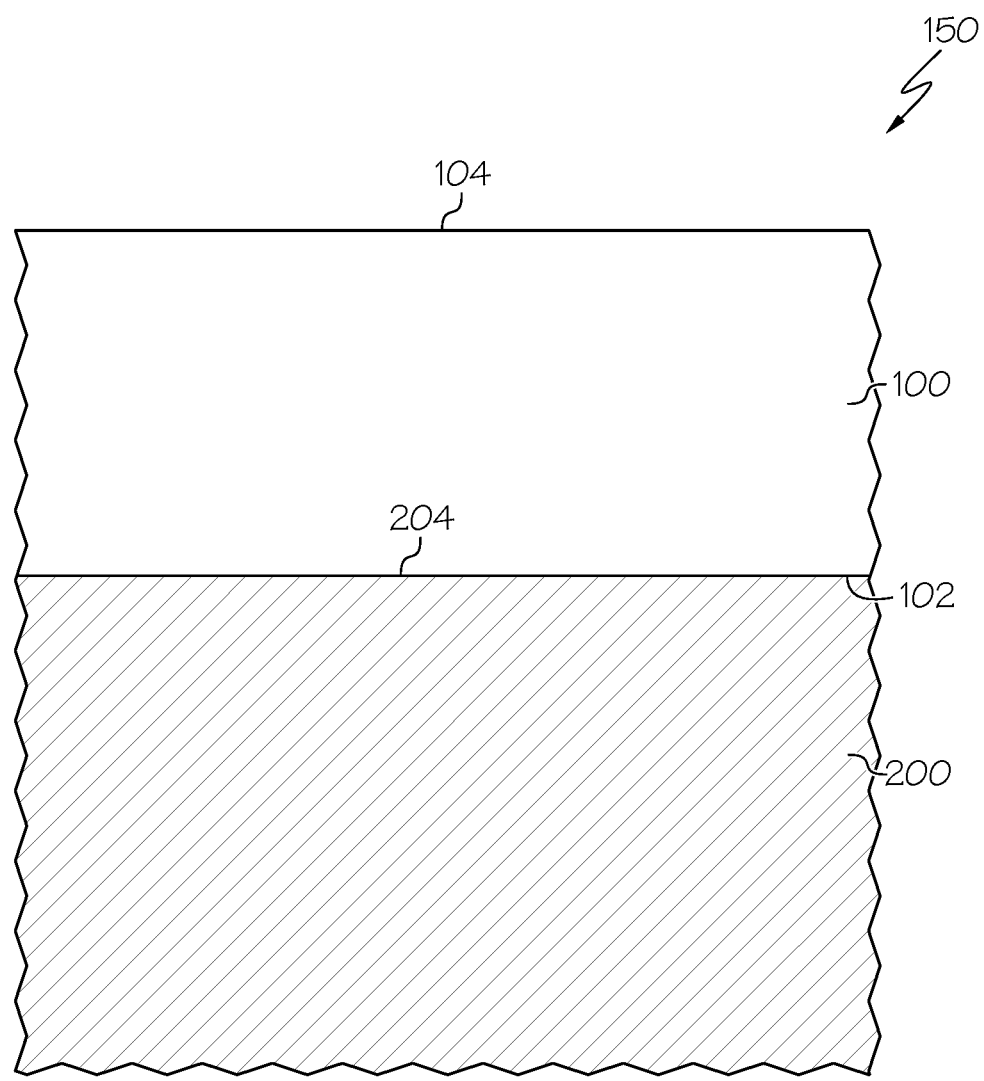
FIG. 1 schematically depicts a cross-sectional view of a substrate comprising a corrosion-resistant film, according to one or more embodiments shown and described herein.

Referring now to FIG. 1, according to one or more embodiments, the corrosion-resistant substrates 150 may comprise a substrate 200 that may comprise at least a first surface 204. The term "substrate" may refer to any object with at least one surface where a solution may contact and form a film that remains on at least a portion of that surface. The corrosion-resistant substrates 150 may also comprise a corrosion-resistant film 100 that comprises at least a first surface 102 and a second surface 104 opposite the first surface 102. The corrosion-resistant film 100 may be positioned on at least a portion of the first surface 204 of the substrate 200. As depicted, the corrosion-resistant substrates 150 may have the first surface 102 of the corrosion-resistant film 100 positioned on and in direct contact with at least a portion of the first surface 204 of the substrate 200. The second surface 104 of the corrosion-resistant film 100 may be an "air-side" surface defining the outer edge of the corrosion-resistant substrate 150.

In one or more embodiments, the corrosion-resistant film 100 is a solid. The term "solid" may refer to a material that is generally firm, stable in shape, and is not a liquid or a fluid. Accordingly, when the corrosion-resistant film 100 is a solid, the first surface 102 of the corrosion-resistant film 100 adheres to the first surface 204 of the substrate 200 so that the corrosion-resistant film 100 remains on the substrate 200 and holds its shape while the substrate 200 and/or the corrosion-resistant film 100 is moved.

In one or more embodiments, the corrosion-resistant film 100 has a thickness of from 0.1 nm to 1,000, such as a thickness of from 0.1 nm to 900 nm, from 0.1 nm to 800 nm, from 0.1 nm to 700 nm, from 0.1 nm to 600 nm, from 0.1 nm to 500 nm, from 0.1 nm to 400 nm, from 0.1 nm to 300 nm, from 0.1 nm to 200 nm, from 0.1 nm to 100 nm, from 1 nm to 1,000 nm, from 10 nm to 1,000 nm, from 50 nm to 1,000 nm, from 100 nm to 1,000 nm, from 200 nm to 1,000 nm, from 300 nm to 1,000 nm, from 400 nm to 1,000 nm, from 500 nm to 1,000 nm, from 600 nm to 1,000 nm, from 700 nm to 1,000 nm, from 800 nm to 1,000 nm, from 900 nm to 1,000 nm, from 10 nm to 900 nm, from 100 nm to 800 nm, from 200 nm to 700 nm, or from 300 nm to 600 nm.

Figure 2:
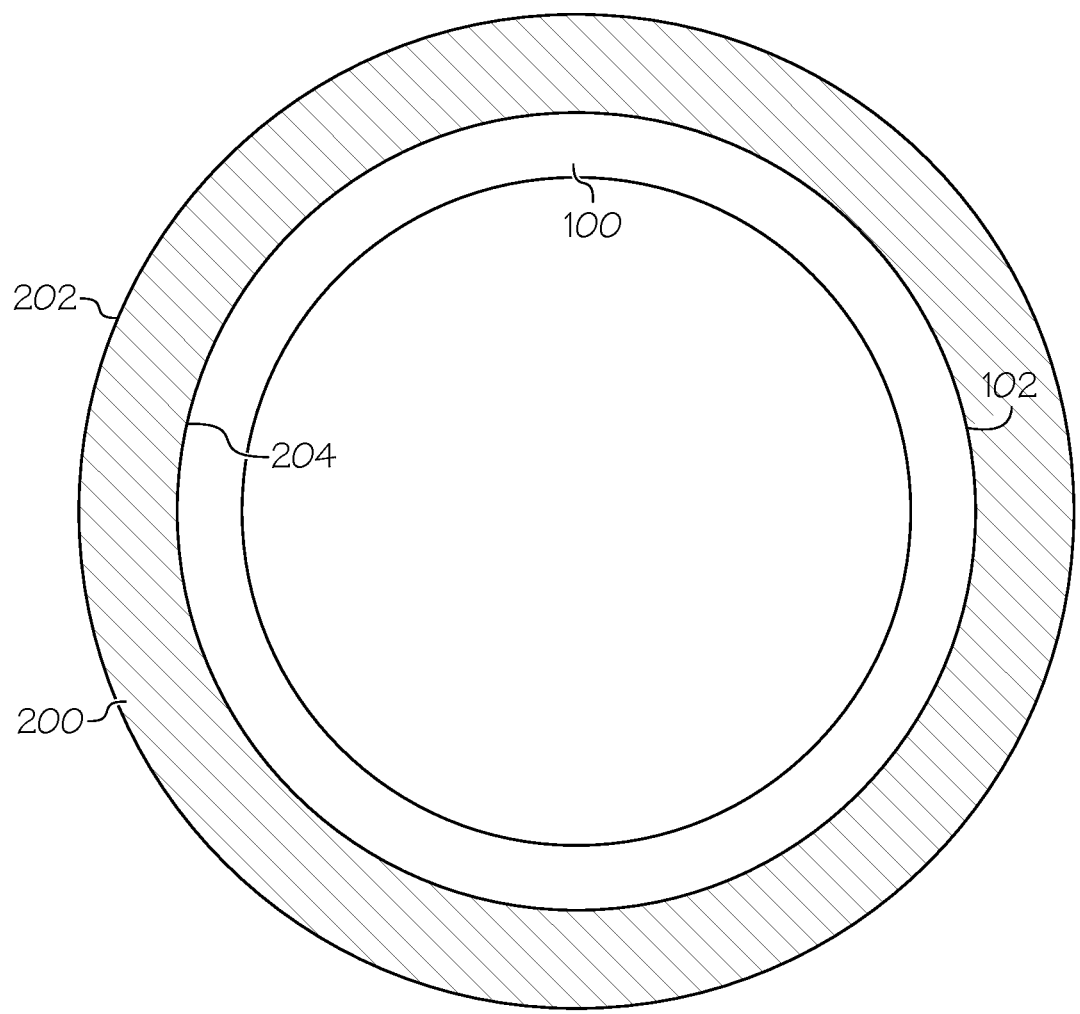
FIG. 2 schematically depicts a cross-sectional view cut in the axial direction of a metal pipe comprising a corrosion-resistant film, according to one or more embodiments shown and described herein.

Now, referring to FIG. 2, in one or more embodiments, the substrate 200 of the corrosion-resistant substrates may be a metal pipe that comprises at least a first surface 204 and a second surface 202. The term "pipe" may refer to a tubular hollow cylinder having a circular, or near circular, cross section that is used to transport substances (for example liquids, gases, slurries, powders, small solids, etc.). The metal pipe may comprise one or more metals and one or more surfaces of the metal pipe may comprise metal oxides. For example, the metal pipe may comprise carbon steel. In some embodiments, the first surface 204 of the metal pipe may be the internal surface of the metal pipe, and the pipe may further comprise an outer surface 202. The term "internal surface" may refer to the surface of the inside of the metal pipe that is enclosed within the tubular cylinder of the metal pipe. For example, when the substrate 200 is a metal pipe and the first surface 204 is the internal surface of the metal pipe, the first surface 102 of the corrosion-resistant film 100 may be in direct contact with the internal surface of the metal pipe. Without being bound by a theory, it is believed that the corrosion-resistant film 100 being in direct contact with a least a portion of the internal surface of the metal pipe creates a barrier between the substances that flow through the metal pipe and the internal surface of the metal pipe.

According to one or more embodiments, the corrosion inhibitor solutions and corrosion-resistant films comprise a bis-quaternized ammonium compound having the structure of Chemical Structure #1.

Chemical Structure #1

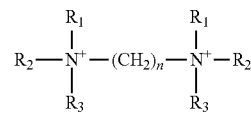

Referring to Chemical Structure #1, the general structure includes $R_1$, $R_2$, and $R_3$ that represent various functional groups that can be included in the bis-quaternized ammonium compound. $R_1$ may be a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group. $R_2$ and $R_3$ may each independently be chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group. The general structure includes "n" that represents the number of —$CH_2$— components that may be present in the alkyl chain that connects the two nitrogen atoms of Chemical Structure #1. The "n" may comprise any integer from 1 to 18. Without being bound by a theory, it is believed that one or more of $R_1$, $R_2$, and $R_3$ having a relatively long carbon chain moiety allows the corrosion-resistant film produced from the corrosion inhibitor solution to better adhere to the surface of a substrate. Further, if the carbon chain moiety has greater than 18 carbon atoms, there is an increased risk of the corrosion-resistant film being removed from the surface of the substrate.

In one or more embodiments, the term "functional group" or "group" may refer to a substituent or moiety that is present in the bis-quaternized ammonium compounds. For example, when the disclosure states that $R_1$ may be a methyl group, the methyl group (—$CH_3$) replaces $R_1$ of Chemical Structure #1 of the bis-quaternized ammonium compound, where the carbon atom of the methyl group is now bonded to the nitrogen atom of the bis-quaternized ammonium compound that $R_1$ was bonded to.

As described herein, moieties may be defined by the number of carbon atoms included in the moiety, such as $C_x$-$C_y$, where x is the least number of carbon atoms and y is the greatest number of carbon atoms contemplated. For example, $C_1$-$C_{10}$ describes a moiety that has from 1 to 10 carbon atoms.

In some embodiments, $R_1$ may be a $C_1$-$C_{10}$ alkyl group. The term "alkyl group" refers to a functional group that only contains carbon and hydrogen atoms where the carbon atoms and hydrogen atoms are only connected by single bonds. In some embodiments, $R_1$ may be a straight chained alkyl group having the chemical formula —$(CH_2)_xCH_3$, where x is from 0 to 9, such as 0 (a methyl group), 1, 2, 3, 4, 5, 6, 7, 8, or 9. In additional embodiments, $R_1$ may be branched alkyl groups having from 3 to 10 carbon atoms, such as 3, 4, 5, 6, 7, 8, 9, or 10 carbon atoms. In some embodiment, the alkyl group may include a ring structure, such as a pentane ring, a hexane ring, etc.

In some embodiments, $R_1$ may be a $C_1$-$C_{10}$ hydroxyl alkyl group. The term "hydroxyl alkyl group" refers to a functional group that includes one or more a hydroxyl moieties (—OH) bonded to an alkyl group. According to embodiments, the hydroxyl alkyl group may include 1, 2, 3, 4, 5, or even more hydroxyl moieties. In some embodiments, $R_1$ may be a straight chained hydroxyl alkyl group having the chemical formula —$(CH_2)_xOH$, where x is from 1 to 10. In additional embodiments, $R_1$ may be branched hydroxyl alkyl groups having from 1 to 10 carbon atoms and at least one hydroxyl group.

In some embodiments, $R_1$ may be a $C_1$-$C_{10}$ alkenyl group. The term "alkenyl group" refers to a functional group consisting of hydrogen and carbon atoms where at least two carbon atoms have a double bond. In some embodiments, the alkenyl group may have a single carbon to carbon double bond that is at the end of moiety (i.e., having the structure —$(CH_2)_xCH=CH_2$, where x is from 0 to 8, such as 0, 1, 2, 3, 4, 5, 6, 7, or 8).

In some embodiments, $R_1$ may be a $C_1$-$C_{10}$ alkynl group. The term "alkynyl group" refers to a functional group consisting of hydrogen and carbon atoms where at least two carbon atoms have a triple bond. In some embodiments, the alkynl group may have a single carbon to carbon triple bond that is at the end of moiety (i.e., having the structure —$(CH_2)_xC≡CH$, where x is from 0 to 8, such as 0, 1, 2, 3, 4, 5, 6, 7, or 8).

In some embodiments, $R_1$ may be a $C_1$-$C_{10}$ acryl group. The term "acryl group" refers to a functional group consisting of a carbon-carbon double bond and a carbon-oxygen double bond separated by a carbon-carbon single bond. The acryl group may have the general formula —$(CH_2)_nCO$-$CHCH_2$, where n is any integer from 0 to 7, such as 0, 1, 2, 3, 4, 5, 6, or 7.

In some embodiments, $R_1$ may be a $C_1$-$C_{10}$ functional alkyl group. The term "functional alkyl group" refers to an alkyl group which includes at least one moiety bonded to any carbon atom of the alkyl group. In some embodiments, the functional alkyl group may comprise more than one of the same moiety. In some embodiments, the functional alkyl group may comprise two or more different moieties. In some embodiments, the functional alkyl group may comprise a moiety chosen form a carboxyl group (i.e., —COOH), an amine group (i.e., —$NH_2$), or a thiol group (i.e., —SH).

In some embodiments, $R_2$ and $R_3$ may, both or independently, be a $C_1$-$C_{18}$ alkyl group. In some embodiments, $R_2$ and $R_3$ may, both or independently, be a straight chained alkyl group having the chemical formula —$(CH_2)_xCH_3$, where x is from 0 to 17, such as 0 (a methyl group), 1, 2, 3, 4, 5, 6, 7, 8, 9, 10, 11, 12, 13, 14, 15, 16, or 17. In additional embodiments, $R_2$ and $R_3$ may, both or independently, be a branched alkyl groups having from 3 to 17 carbon atoms, such as 3, 4, 5, 6, 7, 8, 9, 10, 11, 12, 13, 14, 15, 16, or 17 carbon atoms.

In some embodiments, $R_2$ and $R_3$ may, both or independently, be a $C_1$-$C_{18}$ hydroxyl alkyl group. In some embodiments, $R_2$ and $R_3$ may, both or independently, be a straight chained hydroxyl alkyl group having the chemical formula —$(CH_2)_xOH$, where x is from 1 to 18. In additional embodiments, $R_2$ and $R_3$ may, both or independently, be a branched hydroxyl alkyl group having from 1 to 18 carbon atoms and at least one hydroxyl group.

In some embodiments, $R_2$ and $R_3$ may, both or independently, be a $C_1$-$C_{18}$ alkenyl group. In some embodiments, $R_2$ and $R_3$ may, both or independently, be a $C_1$-$C_{18}$ alkynl group. In some embodiments, $R_2$ and $R_3$ may, both or independently, be a $C_1$-$C_{18}$ acryl group.

In some embodiments, $R_1$ may be a $C_1$-$C_4$ hydroxyl alkyl group or a $C_2$-$C_3$ hydroxyl alkyl group. In some embodiments, $R_1$ may be a $C_1$-$C_4$ alkyl group or a $C_1$-$C_2$ alkyl group. In some embodiments, $R_2$ may be a $C_2$-$C_{12}$ alkyl group, a $C_4$-$C_{10}$ alkyl group, a $C_6$-$C_{10}$ alkyl group, a $C_6$-$C_{14}$ alkyl group, or a $C_{10}$-$C_{14}$ alkyl group. In some embodiments, $R_3$ may be a $C_1$ alkyl group (i.e., a methyl group). In some embodiments, n may be from 2 to 16, from 6 to 16, or from 8 to 14. In one embodiment, $R_1$ may be an ethyl alcohol group (i.e., —$C_2H_5OH$), $R_2$ may be an octyl group (i.e., —$C_8H_{17}$), $R_3$ may be a methyl group (i.e., —$CH_3$), and n may be 12. In another embodiment, $R_1$ may be a methyl group (i.e., —$CH_3$), $R_2$ may be a dodecyl group (i.e., —$C_{12}H_{26}$), $R_3$ may be a methyl group (i.e., —$CH_3$), and n may be 12.

In one or more embodiments, corrosion-resistant film 100 may comprise from 30 wt. % to 80 wt. % of the bis-quaternized ammonium compound. In some embodiments, the corrosion-resistant film 100 may comprise from 30 wt. % to 70 wt. %, from 35 wt. % to 60 wt. %, from 40 wt. % to 60 wt. %, or from 50 wt. % to 60 wt. % of the bis-quaternized ammonium compound. In some embodiments, the corrosion-resistant film 100 may comprise from 30 wt. % to 75 wt. %, from 30 wt. % to 70 wt. %, from 30 wt. % to 65 wt. %, from 30 wt. % to 60 wt. %, from 30 wt. % to 55 wt. %, from 30 wt. % to 50 wt. %, from 30 wt. % to 45 wt. %, from 30 wt. % to 40 wt. %, or from 30 wt. % to 35 wt. % of the bis-quaternized ammonium compound. In some embodiments, the corrosion-resistant film 100 may comprise from 35 wt. % to 80 wt. %, from 40 wt. % to 80 wt. %, from 45 wt. % to 80 wt. %, from 50 wt. % to 80 wt. %, from 55 wt. % to 80 wt. %, from 60 wt. % to 80 wt. %, from 65 wt. % to 80 wt. %, from 70 wt. % to 80 wt. %, or from 75 wt. % to 80 wt. % of the bis-quaternized ammonium compound.

Without being bound by a theory, it is believed that the bis-quaternary ammonium compound has relatively strong bonding to a metal surface due to the physiorption and/or chemisorption of multiple parts of the bis-quaternary ammonium compound and the metal surface. The term "physiorption" refers to the physical bonding of liquid molecules onto a material's surface. Van der Waal interactions, or similar interactions, between atoms on the surface of a metal may cause these surface atoms to be reactive, thus causing them to attract molecules to satisfy the atomic force imbalance. It is believed that the presence of the positively-charged nitrogen atoms of the bis-quaternary ammonium compound forms strong Van der Waal, or similar, interactions with the metal surface. The term "chemisorption" refers to the adsorption between a surface and an adsorbate due to chemical bonding. Multiple parts of the bis-quaternary ammonium compound may bond with the metal surface. It is believed that due to the increased number of functional groups and/or the presence of multiple positively-charged nitrogen atoms of the bis-quaternary ammonium compound that can interact with a metal surface through physiorption and/or chemisorption, the corrosion-resistant film 100 that comprises the bis-quaternary ammonium compound forms stronger interactions and bonds with a metal surface and, thus, provides the metal surface with a stronger and longer lasting corrosion-resistant film 100 than many conventional films that use conventional compounds for resisting corrosion on a metal surface.

In one or more embodiments, the corrosion-resistant film 100 may further comprise, in addition to the bis-quaternized ammonium compound, at least one imidazoline-based compound. According to embodiments, the term "imidazoline-based compound" may refer to a compound that comprises at least one 5-membered cyclic chemical compound that contains two nitrogen atoms, where the nitrogen atoms are the first and third members of the cyclic ring, carbon atoms are the second, fourth, and fifth members of the cyclic ring, and there is one double bond present in the cyclic ring. For example, the corrosion-resistant film 100 may comprise 2-(8-heptadecenyl)-2-imidazoline-1-ethanol. The corrosion-resistant film 100 may comprise from 5 wt. % to 50 wt. % of the imidazoline-based compound. In some embodiments, the corrosion-resistant film 100 may comprise from 10 wt. % to 40 wt. %, from 10 wt. % to 35 wt. %, from 15 wt. % to 30 wt. %, or from 15 wt. % to 25 wt. % of the imidazoline-based compound. In some embodiments, the corrosion-resistant film 100 may comprise from 5 wt. % to 45 wt. %, from 5 wt. % to 40 wt. %, from 5 wt. % to 35 wt. %, from 5 wt. % to 30 wt. %, from 5 wt. % to 25 wt. %, from 5 wt. % to 20 wt. %, from 5 wt. % to 15 wt. %, or from 5 wt. % to 10 wt. % of the imidazoline-based compound. In some embodiments, the corrosion-resistant film 100 may comprise from 10 wt. % to 50 wt. %, 15 wt. % to 50 wt. %, 20 wt. % to 50 wt. %, 25 wt. % to 50 wt. %, 30 wt. % to 50 wt. %, 35 wt. % to 50 wt. %, 40 wt. % to 50 wt. %, or 45 wt. % to 50 wt. % of the imidazoline-based compound. Without being bound by a theory, it is believed that the imidazoline-based compound is able to demonstrate relatively strong bonding to a metal surface due to both the physiorption and chemisorption of the metal surface and multiple parts of the imidazoline-based compound including, but not limited to, the nitrogen atoms of the cyclic ring, the long alkyl chains (i.e., $C_{3+}$ alkyl chains) that may be bonded to any atom of the cyclic ring, and various functional groups that may be bonded to the long alkyl chains.

In one or more embodiments, the corrosion-resistant film 100 may comprise a synergist. In some embodiments, the corrosion-resistant film 100 may comprise more than one synergist. The term "synergist" may refer to a chemical compound that increases the corrosion-resistant activity of the imidazoline-based compound and bis-quaternized ammonium compound in the corrosion-resistant film 100. For example, the synergist may comprise thioglycolic acid, 2-mercaptoethanol, or combinations thereof. According to embodiments, the corrosion-resistant film 100 may comprise from 5 wt. % to 40 wt. % of the synergist. In some embodiments, the corrosion-resistant film 100 may comprise from 10 wt. % to 35 wt. %, from 15 wt. % to 30 wt. %, or from 15 wt. % to 25 wt. % of the synergist. In some embodiments, the corrosion-resistant film 100 may comprise from 5 wt. % to 35 wt. %, 5 wt. % to 30 wt. %, 5 wt. % to 25 wt. %, 5 wt. % to 20 wt. %, 5 wt. % to 15 wt. %, or 5 wt. % to 10 wt. %, of the synergist. In some embodiments, the corrosion-resistant film 100 may comprise from 10 wt. % to 40 wt. %, 15 wt. % to 40 wt. %, 20 wt. % to 40 wt. %, 25 wt. % to 40 wt. %, 30 wt. % to 40 wt. %, or 35 wt. % to 40 wt. % of the synergist. Without being bound by a theory, it is believed that the synergist may bind to a metal surface due to its high electron density and help the bis-quaternized ammonium compound bond with the metal surface in order to provide a more effective physical barrier between the metal surface and substances surrounding the metal surface.

In one or more embodiments, the corrosion-resistant film 100 may comprise a surfactant. In some embodiments, the corrosion-resistant film 100 may comprise more than one surfactant. The term "surfactant" may refer to a compound that lowers the surface tension (or interfacial tension) between two liquids, between a gas and a liquid, or between a liquid and a solid. For example, the surfactant may be a long chained ethoxylated alcohol. According to embodiments, the corrosion-resistant film 100 may comprise from 1 wt. % to 5 wt. % of the surfactant. In some embodiments, the corrosion-resistant film 100 may comprise from 1.5 wt. % to 4 wt. %, from 1.5 wt. % to 3 wt. %, or from 1.5 wt. % to 2.5 wt. % of the surfactant. In some embodiments, the corrosion-resistant film 100 may comprise from 1 wt. % to 4.5 wt. %, from 1 wt. % to 4 wt. %, from 1 wt. % to 3.5 wt. %, from 1 wt. % to 3 wt. %, from 1 wt. % to 2.5 wt. %, from 1 wt. % to 2 wt. %, or from 1 wt. % to 1.5 wt. % of the surfactant. In some embodiments, the corrosion-resistant film 100 may comprise from 1.5 wt. % to 5 wt. %, 2 wt. % to 5 wt. %, 2.5 wt. % to 5 wt. %, 3 wt. % to 5 wt. %, 3.5 wt. % to 5 wt. %, 4 wt. % to 5 wt. %, or 4.5 wt. % to 5 wt. %, of the surfactant. Without being bound by a theory, it is believed that a surfactant may possess a hydrophilic section that may bond with a metal surface and a lipophilic section that may bond with oil, or similar, compounds and prevent the oil, or similar, compounds from interacting with the metal surface.

In one or more embodiments, the corrosion-resistant film 100 may comprise an ethoxylated amine. In some embodiments, the corrosion-resistant film 100 may comprise more than one ethoxylated amine. The term "ethoxylated amine" may refer to a chemical compound that comprises a nitrogen atom with a —$(CH_2CH_2O)_xH$ functional group and a —$(CH_2CH_2O)_yH$ functional group bonded to the nitrogen atom, where x and y is any integer greater than or equal to 1. For example, the ethoxylated amine may comprise 2-2-(2-hydroxyethoxy)ethylaminoethanol. According to some embodiments, the corrosion-resistant film 100 may comprise from 1 wt. % to 10 wt. % of the ethoxylated amine. In some embodiments, the corrosion-resistant film 100 may comprise from 2 wt. % to 8 wt. %, from 2.5 wt. % to 7 wt. %, or from 3 wt. % to 5 wt. % of the ethoxylated amine. In some embodiments, the corrosion-resistant film 100 may comprise from 2 wt. % to 10 wt. %, from 3 wt. % to 10 wt. %, from 4 wt. % to 10 wt. %, from 5 wt. % to 10 wt. %, from 6 wt. % to 10 wt. %, from 7 wt. % to 10 wt. %, from 8 wt. % to 10 wt. %, or from 9 wt. % to 10 wt. % of the ethoxylated amine. In some embodiments, the corrosion-resistant film 100 may comprise from 1 wt. % to 9 wt. %, from 1 wt. % to 8 wt. %, from 1 wt. % to 7 wt. %, from 1 wt. % to 6 wt. %, from 1 wt. % to 5 wt. %, from 1 wt. % to 4 wt. %, from 1 wt. % to 3 wt. %, or from 1 wt. % to 2 wt. % of the ethoxylated amine. Without being bound by a theory, it is believed that an ethoxylated amine may promote better film formation and react with anodic or cathodic reaction sites of corrosive materials in order to slow down the oxidation or reduction reactions between a metal surface and corrosive materials.

In one or more embodiments, the corrosion-resistant film 100 may comprise a coupling agent. In some embodiments, the corrosion-resistant film 100 may comprise more than one coupling agent. The term "coupling agent" may refer to a chemical that can enhance adhesion or bonding between a surface and a polymer matrix. For example, the coupling agent may be an alkyl dipropionic acid sodium salt. According to some embodiments, the corrosion-resistant film 100 may comprise from 2 wt. % to 8 wt. %, from 2.5 wt. % to 7 wt. %, or from 3 wt. % to 5 wt. % of the coupling agent. In some embodiments, the corrosion-resistant film 100 may comprise from 2 wt. % to 10 wt. %, from 3 wt. % to 10 wt. %, from 4 wt. % to 10 wt. %, from 5 wt. % to 10 wt. %, from 6 wt. % to 10 wt. %, from 7 wt. % to 10 wt. %, from 8 wt. % to 10 wt. %, or from 9 wt. % to 10 wt. % of the coupling agent. In some embodiments, the corrosion-resistant film 100 may comprise from 1 wt. % to 9 wt. %, from 1 wt. % to 8 wt. %, from 1 wt. % to 7 wt. %, from 1 wt. % to 6 wt. %, from 1 wt. % to 5 wt. %, from 1 wt. % to 4 wt. %, from 1 wt. % to 3 wt. %, or from 1 wt. % to 2 wt. % of the coupling agent. Without being bound by a theory, it is believed that a coupling agent avoids phase separation of components in the corrosion-resistant films due to changes in temperature.

The present disclosure is also directed to methods of producing corrosion-resistant substrates 150 and corrosion inhibitor solutions. The methods of producing corrosion-resistant substrates 150 comprise contacting at least a portion of a first surface 204 of a substrate 200 with a corrosion inhibitor solution, where the corrosion inhibitor solution comprises a solvent and the bis-quaternized ammonium compound described herein. Then, the methods further comprise drying the corrosion inhibitor solution to produce the corrosion-resistant film 100 on the substrate 200, where at least a portion of the solvent is expelled from the corrosion inhibitor solution during the drying to form the solid corrosion-resistant film 100. For example, when the substrate 200 is a pipe and the first surface 204 is the internal surface of the pipe, the corrosion inhibitor solution is adhered on the internal surface of the pipe and the corrosion inhibitor solution dries on the internal surface of the pipe to form the solid corrosion-resistant film 100 on the internal surface of the pipe.

In one or more embodiments, the corrosion inhibitor solution may comprise a solvent, a bis-quaternized ammonium compound, an imidazoline-based compound, a synergist, a surfactant, an ethoxylated amine, and/or a coupling agent as described herein. In some embodiments, the solvent may comprise water, ethylene glycol, ethylene diamine, or combinations thereof.

According to one or more embodiments, the corrosion inhibitor solution may comprise from 50 wt. % to 90 wt. % of the solvent. In some embodiments, the corrosion inhibitor solution may comprise from 55 wt. % to 85 wt. %, from 65 wt. % to 85 wt. %, or from 70 wt. % to 80 wt. % of the solvent. In some embodiments, the corrosion inhibitor solution may comprise from 50 wt. % to 85 wt. %, from 50 wt. % to 80 wt. %, from 50 wt. % to 75 wt. %, from 50 wt. % to 70 wt. %, from 50 wt. % to 65 wt. %, from 50 wt. % to 60 wt. %, or from 50 wt. % to 55 wt. % of the solvent. In some embodiments, the corrosion inhibitor solution may comprise from 55 wt. % to 90 wt. %, from 60 wt. % to 90 wt. %, from 65 wt. % to 90 wt. %, from 70 wt. % to 90 wt. %, from 75 wt. % to 90 wt. %, from 80 wt. % to 90 wt. %, or from 85 wt. % to 90 wt. % of the solvent.

According to one or more embodiments, the corrosion inhibitor solution may comprise from 1 wt. % to 20 wt. % of the bis-quaternized ammonium compound. In some embodiments, the corrosion inhibitor solution may comprise from 2 wt. % to 18 wt. %, from 6 wt. % to 18 wt. %, or from 8 wt. % to 16 wt. % of the bis-quaternized ammonium compound. In some embodiments, the corrosion inhibitor solution may comprise from 1 wt. % to 18 wt. %, 1 wt. % to 16 wt. %, 1 wt. % to 14 wt. %, 1 wt. % to 12 wt. %, 1 wt. % to 10 wt. %, 1 wt. % to 8 wt. %, 1 wt. % to 6 wt. %, 1 wt. % to 4 wt. %, or 1 wt. % to 2 wt. % of the bis-quaternized ammonium compound. In some embodiments, the corrosion inhibitor solution may comprise from 2 wt. % to 20 wt. %, from 4 wt. % to 20 wt. %, from 6 wt. % to 20 wt. %, from 8 wt. % to 20 wt. %, from 10 wt. % to 20 wt. %, from 12 wt. % to 20 wt. %, from 14 wt. % to 20 wt. %, from 16 wt. % to 20 wt. %, or from 18 wt. % to 20 wt. % of the bis-quaternized ammonium compound.

According to one or more embodiments, the corrosion inhibitor solution may comprise from 1 wt. % to 20 wt. % of the imidazoline-based compound. In some embodiments, the corrosion inhibitor solution may comprise from 1 wt. % to 15 wt. %, from 2 wt. % to 10 wt. %, or from 2.5 wt. % to 7.5 wt. % of the imidazoline-based compound. In some embodiments, the corrosion inhibitor solution may comprise from 1 wt. % to 18 wt. %, 1 wt. % to 16 wt. %, 1 wt. % to 14 wt. %, 1 wt. % to 12 wt. %, 1 wt. % to 10 wt. %, 1 wt. % to 8 wt. %, 1 wt. % to 6 wt. %, 1 wt. % to 4 wt. %, or 1 wt. % to 2 wt. % of the imidazoline-based compound. In some embodiments, the corrosion inhibitor solution may comprise from 2 wt. % to 20 wt. %, from 4 wt. % to 20 wt. %, from 6 wt. % to 20 wt. %, from 8 wt. % to 20 wt. %, from 10 wt. % to 20 wt. %, from 12 wt. % to 20 wt. %, from 14 wt. % to 20 wt. %, from 16 wt. % to 20 wt. %, or from 18 wt. % to 20 wt. % of the imidazoline-based compound.

According to one or more embodiments, the corrosion inhibitor solution may comprise from 0.1 wt. % to 5 wt. % of, independently or in combination, the surfactant, the ethoxylated amine, and the coupling agent. In some embodiments, the corrosion inhibitor solution may comprise from 0.2 wt. % to 2.5 wt. %, from 0.25 wt. % to 1.5 wt. %, or from 0.3 wt. % to 1 wt. % of, independently or in combination, the surfactant, the ethoxylated amine, and the coupling agent. In some embodiments, the corrosion inhibitor solution may comprise from 0.5 wt. % to 5 wt. %, from 1 wt. % to 1.5 wt. %, from 1.5 wt. % to 5 wt. %, from 2 wt. % to 5 wt. %, from 2.5 wt. % to 5 wt. %, from 3 wt. % to 5 wt. %, from 3.5 wt. % to 5 wt. %, from 4 wt. % to 5 wt. %, or from 4.5 wt. % to 5 wt. % of, independently or in combination, the surfactant, the ethoxylated amine, and the coupling agent. In some embodiments, the corrosion inhibitor solution may comprise from 0.1 wt. % to 4.5 wt. %, from 0.1 wt. % to 4 wt. %, from 0.1 wt. % to 3.5 wt. %, from 0.1 wt. % to 3 wt. %, from 0.1 wt. % to 2.5 wt. %, from 0.1 wt. % to 2 wt. %, from 0.1 wt. % to 1.5 wt. %, or from 0.1 wt. % to 1 wt. % of, independently or in combination, the surfactant, the ethoxylated amine, and the coupling agent.

In some embodiments, drying the corrosion inhibitor solution in order to produce the solid corrosion-resistant film 100 may include passively drying the corrosion inhibitor solution. Passively drying the corrosion inhibitor solution may refer to allowing the corrosion inhibitor solution to dry on the first surface 204 of the substrate 200 without the use of an external heat source. For example, the corrosion inhibitor solution may be allowed to dry at room temperature after contacting the first surface 204 of the substrate 200 or any similar method where the corrosion inhibitor solution is not heated with an external heat source. Further, drying the corrosion inhibitor solution in order to produce the solid corrosion-resistant film 100 may include heating the corrosion inhibitor solution with a heat source. Heating the corrosion inhibitor solution with a heat source may refer to any method where heat from an outside source is transferred to the corrosion inhibitor solution and the first surface 204 of the substrate 200 in order to dry the corrosion inhibitor solution. For example, a heat lamp may be directed onto the corrosion inhibitor solution and the first surface 204 of the substrate 200 in order to accelerate the drying time of the corrosion inhibitor solution. In another example, external processing units, liquids, or gases may transfer heat to the corrosion inhibitor solution and the first surface 204 of the substrate 200 in order to accelerate the drying time of the corrosion inhibitor solution. In some embodiments, the drying of the corrosion inhibitor solution in order to produce the solid corrosion-resistant film 100 may include both passively drying the corrosion inhibitor solution and heating the corrosion inhibitor solution with a heat source.

EXAMPLES

Examples are provided herein which may disclose one or more embodiments of the present disclosure. However, the Examples should not be viewed as limiting on the claimed embodiments hereinafter provided.

Example 1

Synthesis of Sample A Bis-Quaternary Ammonium Salt Compound

Figure 3:
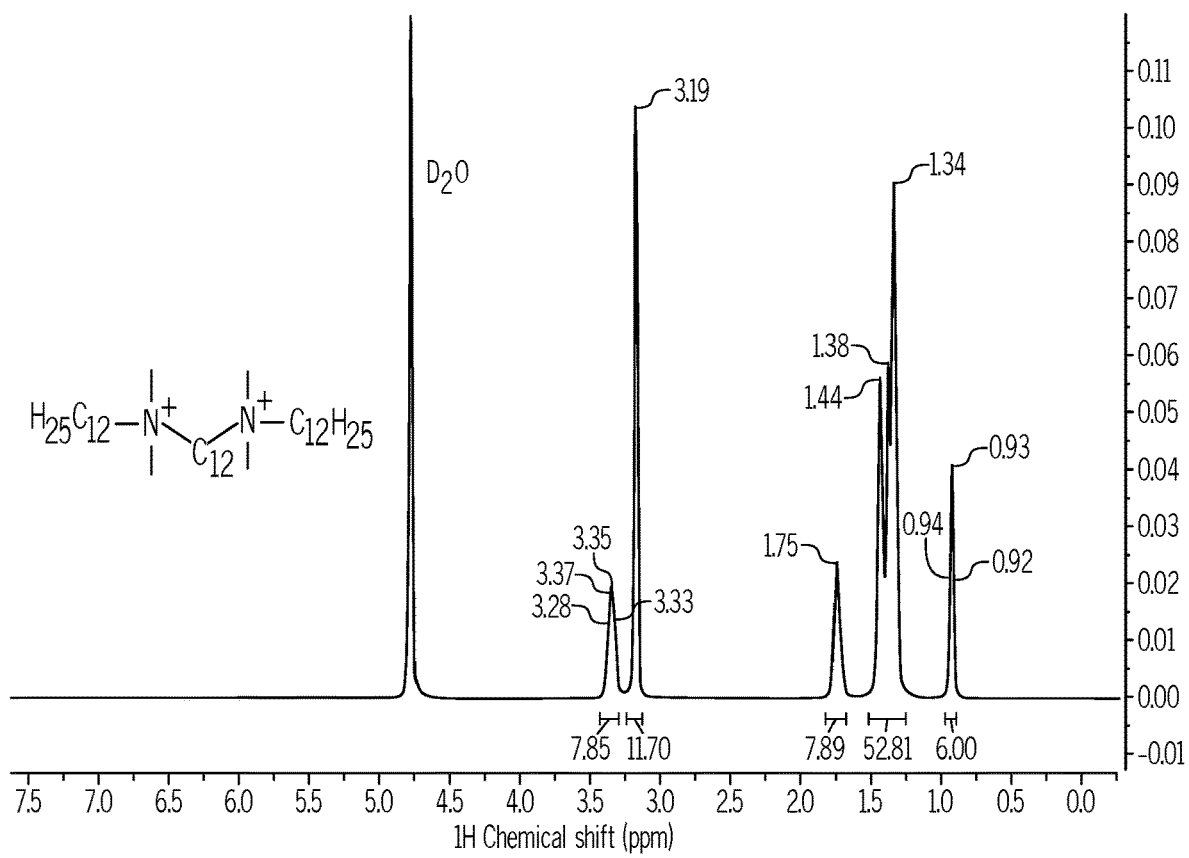
FIG. 3 graphically depicts the H-NMR spectrum of a synthesized bis-quaternary ammonium compound, according to one or more embodiments shown and described herein.

A solution of N,N-dimethyldodecylamine (3.78 grams, 24 mmol), 1,12-dibromododecane (3.28 grams, 10 mmol), and acetonitrile (50 mL) was added to a closed vessel and heated at 80° C. for 12 hours. After removing the acetonitrile, the residual solid was repeatedly washed with ether to obtain the final solid bis-quaternary ammonium salt compound, referred to herein as Sample A (6.0 grams, 93%). FIG. 3 provides the H-NMR spectra of this Sample A compound.

Example 2

Synthesis of Sample B Bis-Quaternary Ammonium Salt Compound

Figure 4:
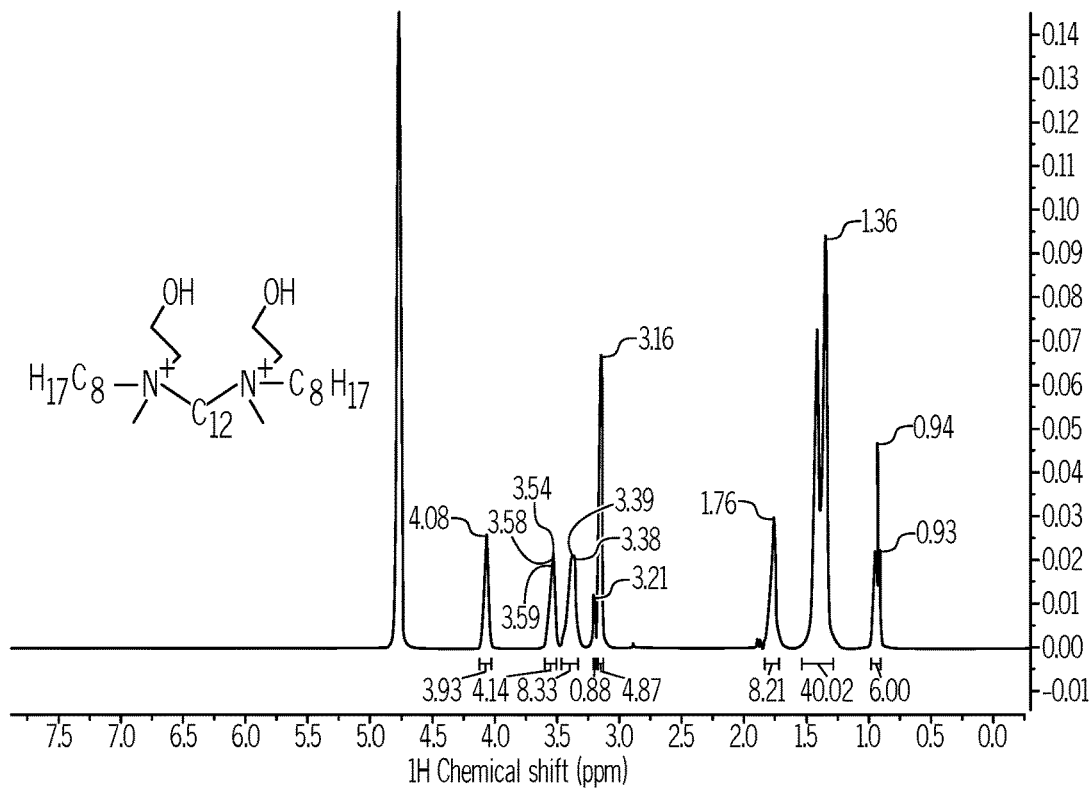
FIG. 4 graphically depicts the H-NMR spectrum of another synthesized bis-quaternary ammonium compound, according to one or more embodiments shown and described herein.

A solution of N-methylethanolamine (4.43 grams, 59 mmol), octyl bromide (5.156 grams, 26.7 mmol), acetonitrile (50 mL), and $K_2CO_3$ (6 grams) was added to a round bottom flask and heated under reflux at 70° C. for 12 hours. After removing the acetonitrile, the residual was washed using 20 mL of $H_2O$ and 200 mL of diethyl ether. Then, the diethyl ether layer was removed to obtain N-methyl, N-ethanol octylamine (4.53 grams, 93%) as a light-yellow liquid. A solution of N-methyl, N-ethanol octylamine (2.25 grams, 12 mmol), 1,12-dibromododecane (1.64 grams, 5 mmol), and acetonitrile (15 mL) was added to another round bottom flask and was heated under reflux at 80° C. for 12 hours. After removing the acetonitrile, the residual brown viscous liquid was washed with ether multiple times to obtain a bis-quaternary ammonium solid, referred to as Sample B (3.0 grams, 85%). FIG. 4 provides the H-NMR spectra of this Sample B compound.

Example 3

A corrosion inhibitor solution was prepared. The following table, Table 1, discloses a corrosion inhibitor solution composition that comprises the bis-quaternary ammonium solids Sample A or Sample B, among other components, that was used for performance evaluation and comparison with a commercial corrosion inhibitor.

TABLE 1

| Component Function | Components Name | Weight % |
|---|---|---|
| Solvent | Water | 70.4 |
| Synergist | Thioglycolic Acid | 2.8 |
| | 2-Mercaptoethanol | 1.5 |
| Secondary Solvents | Ethylene Glycol | 1.5 |
| | Ethylene Diamine | 1.5 |
| Supporting Components | Surfactant (Nonionic) | 0.5 |
| | Ethoxylated Amine | 0.9 |
| | Coupling Agent | 0.9 |
| Corrosion-Resistant Compound | Imidazoline | 5.0 |
| | Sample A or Sample B | 15.0 |
| | Total | 100.0 |

Example 4

A High-Temperature and High-Pressure (HTHP) autoclave rotating cage was used to conduct the corrosion tests under simulated and controlled dynamic field conditions. A four-liter reactor was constructed from C-276 alloy, which was capable of withstanding a harsh corrosive environment. The test material was carbon steel coupons and the coupons were cleaned and degreased before and after testing. The coupons were positioned in a fixed cage made out of polyetheretherketone (PEEK) material and then mounted in the autoclave.

The autoclave was purged with $N_2$ to remove dissolved oxygen. The autoclave was then pressurized with the required gases ($H_2S$ and $CO_2$). The autoclave was heated to the required test temperature (182° F.). A kerosene and water (1:1) mixture was stirred at room temperature with 10 ppm of the Sample A or Sample B. After 2 hours, the kerosene was removed and the remaining water was used in the autoclave for the final test. The final pressure was maintained at the required pressure (250 psi) using high purity nitrogen gas. In all the tests, the corrosion inhibitor solutions were injected immediately after fixing the coupons in the autoclave. The corrosion rate and inhibition efficiency of the samples were calculated using a weight loss by the following equation 1 and 2:

$$\text{Corrosion rate(CR)(MPY)} = \Delta W*22{,}300/D*A*T \quad (1)$$

$$\text{Inhibition efficiency(IE \%)} = (CR_{blank} - CR_{inhibitor})*100/CR_{blank} \quad (2)$$

where $\Delta W$ is the weight loss of coupon in mg, D is the density of the standard mild steel coupon (C-1018) (7.89 g/cm$^3$), A is an area of the exposed coupon (7.86 square inches) and T is the exposure time (one day). The MPY unit means mg of coupon material lost per year. For equation 2, $CR_{blank}$ is the corrosion rate measured for the carbon steel coupons without the corrosion-resistant film and $CR_{inhibitor}$ is the corrosion rate measured for the carbon steel coupons with the corrosion-resistant film.

The corrosion inhibition efficiency and corrosion rate of a commercial corrosion inhibitor, including alkyl pyridine benzyl chloride, and the disclosed corrosion-resistant films are shown below in Table 2. The disclosed corrosion-resistant films have a lower corrosion rate and a higher corrosion inhibition efficiency than the commercial/conventional corrosion inhibitor used in gas oil separation plants (GOSPs) for a wet sour environment in the oil and gas industry.

TABLE 2

| | Inhibition Efficiency (%) at 10 ppm | Corrosion Rate (MPY) at 10 ppm |
|---|---|---|
| Commercial Corrosion Inhibitor | 50 | 8.1 |
| Disclosed Corrosion-Resistant Film that includes Sample A | 63.6 | 6.9 |
| Disclosed Corrosion-Resistant Film that includes Sample B | 53.5 | 7.5 |

The present disclosure includes one or more non-limiting aspects. A first aspect includes a corrosion-resistant substrate comprising a substrate comprising a first surface; and a corrosion-resistant film positioned on at least a portion of the first surface of the substrate, wherein the corrosion-resistant film is solid, and wherein the corrosion-resistant film comprises a bis-quaternized ammonium compound having a general formula:

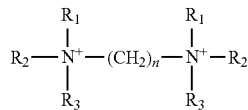

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18.

A second aspect includes any above aspect, wherein the $C_1$-$C_{10}$ functional alkyl group comprises a moiety chosen from a carboxyl group, an amine group, or a thiol group.

A third aspect includes any above aspect, wherein the first surface is metal or metal oxide.

A fourth aspect includes any above aspect, wherein the substrate is a metal pipe and the first surface is an internal surface of the metal pipe.

A fifth aspect includes any above aspect, wherein the corrosion-resistant film comprises from 30 wt. % to 80 wt. % of the bis-quaternized ammonium compound.

A sixth aspect includes any above aspect, wherein the corrosion-resistant film further comprises one or more of a synergist, a surfactant, an ethoxylated amine, or a coupling agent.

A seventh aspect includes any above aspect, wherein the corrosion-resistant film comprises from 5 wt. % to 40 wt. % of the synergist.

An eighth aspect includes any above aspect, wherein the corrosion-resistant film comprises from 1 wt. % to 5 wt. % of the surfactant.

A ninth aspect includes any above aspect, wherein the corrosion-resistant film comprises from 1 wt. % to 10 wt. % of the ethoxylated amine.

A tenth aspect includes any above aspect, wherein the corrosion-resistant film comprises from 1 wt. % to 10 wt. % of the coupling agent.

An eleventh aspect includes any above aspect, wherein $R_1$ is an ethyl alcohol group, $R_2$ is an octyl group, $R_3$ is a methyl group, and n is 12.

A twelfth aspect includes any above aspect, wherein $R_1$ is a methyl group, $R_2$ is a dodecyl group, $R_3$ is a methyl group, and n is 12.

A thirteenth aspect includes a method of producing a corrosion-resistant substrate, the method comprising: contacting at least a portion of a first surface of a substrate with a corrosion inhibitor solution, wherein the corrosion inhibitor solution comprises a solvent and a bis-quaternized ammonium compound having a general formula:

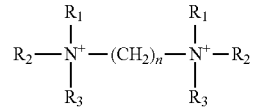

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18; and drying the corrosion inhibitor solution to produce the corrosion-resistant film on the substrate, wherein at least a portion of the solvent is expelled from the corrosion inhibitor solution during the drying to form the corrosion-resistant film, such that the corrosion-resistant film is solid.

A fourteenth aspect includes any above aspect, wherein the $C_1$-$C_{10}$ functional alkyl group comprises a moiety chosen from a carboxyl group, an amine group, or a thiol group.

A fifteenth aspect includes any above aspect, wherein the solvent comprises one or more of water, ethylene glycol, or ethylene diamine.

A sixteenth aspect includes any above aspect, wherein the first surface is metal or metal oxide.

A seventeenth aspect includes any above aspect, wherein the substrate is a metal pipe and the first surface is an internal surface of the metal pipe.

An eighteenth aspect includes any above aspect, wherein $R_1$ is an ethyl alcohol group, $R_2$ is an octyl group, $R_3$ is a methyl group, and n is 12.

A nineteenth aspect includes any above aspect, wherein $R_1$ is a methyl group, $R_2$ is a dodecyl group, $R_3$ is a methyl group, and n is 12.

A twentieth aspect includes a corrosion inhibitor solution, wherein the corrosion inhibitor solution comprises a solvent and a bis-quaternized ammonium compound having a general formula:

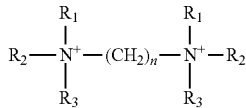

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group; wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

It is also noted that recitations herein of "at least one" component, element, etc., should not be used to create an inference that the alternative use of the articles "a" or "an" should be limited to a single component, element, etc.

For the purposes of describing and defining the presently disclosed technology it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

What is claimed is:

1. A corrosion-resistant substrate comprising:
   a substrate comprising a first surface; and
   a corrosion-resistant film positioned on at least a portion of the first surface of the substrate, wherein the corrosion-resistant film is solid, and wherein the corrosion-resistant film comprises a bis-quaternized ammonium compound having a general formula:

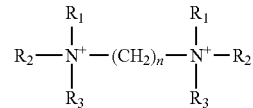

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group;
   wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and
   wherein n is an integer from 1 to 18.

2. The corrosion-resistant substrate of claim 1, wherein the $C_1$-$C_{10}$ functional alkyl group comprises a moiety chosen from a carboxyl group, an amine group, or a thiol group.

3. The corrosion-resistant substrate of claim 1, wherein the first surface is metal or metal oxide.

4. The corrosion-resistant substrate of claim 1, wherein the substrate is a metal pipe and the first surface is an internal surface of the metal pipe.

5. The corrosion-resistant substrate of claim 1, wherein the corrosion-resistant film comprises from 30 wt. % to 80 wt. % of the bis-quaternized ammonium compound.

6. The corrosion-resistant substrate of claim 1, wherein the corrosion-resistant film further comprises one or more of a synergist, a surfactant, an ethoxylated amine, or a coupling agent.

7. The corrosion-resistant substrate of claim 6, wherein the corrosion-resistant film comprises from 5 wt. % to 40 wt. % of the synergist.

8. The corrosion-resistant substrate of claim 6, wherein the corrosion-resistant film comprises from 1 wt. % to 5 wt. % of the surfactant.

9. The corrosion-resistant substrate of claim 6, wherein the corrosion-resistant film comprises from 1 wt. % to 10 wt. % of the ethoxylated amine.

10. The corrosion-resistant substrate of claim 6, wherein the corrosion-resistant film comprises from 1 wt. % to 10 wt. % of the coupling agent.

11. The corrosion-resistant substrate of claim 1, wherein $R_1$ is an ethyl alcohol group, $R_2$ is an octyl group, $R_3$ is a methyl group, and n is 12.

12. The corrosion-resistant substrate of claim 1, wherein $R_1$ is a methyl group, $R_2$ is a dodecyl group, $R_3$ is a methyl group, and n is 12.

13. A method of producing a corrosion-resistant substrate, the method comprising:

contacting at least a portion of a first surface of a substrate with a corrosion inhibitor solution, wherein the corrosion inhibitor solution comprises a solvent and a bis-quaternized ammonium compound having a general formula:

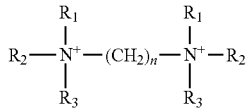

wherein $R_1$ is an a $C_1$-$C_{10}$ alkyl group, a $C_1$-$C_{10}$ hydroxyl alkyl group, a $C_1$-$C_{10}$ alkenyl group, a $C_1$-$C_{10}$ alkynl group, a $C_1$-$C_{10}$ acryl group, a $C_1$-$C_{10}$ cycloalkyl group, or a $C_1$-$C_{10}$ functional alkyl group;

wherein $R_2$ and $R_3$ are each independently chosen from a $C_1$-$C_{18}$ alkyl group, a $C_1$-$C_{18}$ hydroxyl alkyl group, a $C_1$-$C_{18}$ alkenyl group, a $C_1$-$C_{18}$ alkynl group, or a $C_1$-$C_{18}$ acryl group; and wherein n is an integer from 1 to 18; and drying the corrosion inhibitor solution to produce the corrosion-resistant film on the substrate, wherein at least a portion of the solvent is expelled from the corrosion inhibitor solution during the drying to form the corrosion-resistant film, such that the corrosion-resistant film is solid.

14. The method of claim 13, wherein the $C_1$-$C_{10}$ functional alkyl group comprises a moiety chosen from a carboxyl group, an amine group, or a thiol group.

15. The method of claim 13, wherein the solvent comprises one or more of water, ethylene glycol, or ethylene diamine.

16. The method of claim 13, wherein the first surface is metal or metal oxide.

17. The method of claim 13, wherein the substrate is a metal pipe and the first surface is an internal surface of the metal pipe.

18. The method of claim 13, wherein $R_1$ is an ethyl alcohol group, $R_2$ is an octyl group, $R_3$ is a methyl group, and n is 12.

19. The method of claim 13, wherein $R_1$ is a methyl group, $R_2$ is a dodecyl group, $R_3$ is a methyl group, and n is 12.

* * * * *

UNITED STATES PATENT AND TRADEMARK OFFICE
CERTIFICATE OF CORRECTION

PATENT NO. : 12,065,582 B2
APPLICATION NO. : 17/742004
DATED : August 20, 2024
INVENTOR(S) : Ul-Haq et al.

It is certified that error appears in the above-identified patent and that said Letters Patent is hereby corrected as shown below:

In the Specification

In Column 2, Line(s) 12, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In Column 2, Line(s) 41, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In Column 2, Line(s) 60, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In Column 14, Line(s) 1, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In Column 14, Line(s) 58, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In Column 15, Line(s) 33, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

In the Claims

Claim 1, Column 16, Line(s) 35, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

Claim 13, Column 17, Line(s) 25, delete "wherein $R_1$ is an a $C_1$-$C_{10}$ alkyl group, a $C_1$-$C_{10}$ hydroxyl" and insert --wherein $R_1$ is a $C_1$-$C_{10}$ alkyl group, a $C_1$-$C_{10}$ hydroxyl--.

Signed and Sealed this
Twelfth Day of November, 2024

Katherine Kelly Vidal
*Director of the United States Patent and Trademark Office*